United States Patent
Candelario et al.

(10) Patent No.: US 12,008,129 B2
(45) Date of Patent: *Jun. 11, 2024

(54) SECURE CREDENTIALING SYSTEMS AND METHODS

(71) Applicant: PRACTICE INTERACTIVE, INC., Austin, TX (US)

(72) Inventors: Alexander Candelario, Austin, TX (US); Shawn Frasquillo, Canyon Lake, TX (US); Garry McIntosh, San Marcos, TX (US)

(73) Assignee: PRACTICE INTERACTIVE, INC., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/105,871

(22) Filed: Feb. 5, 2023

(65) Prior Publication Data

US 2023/0252176 A1 Aug. 10, 2023

Related U.S. Application Data

(63) Continuation of application No. 16/939,037, filed on Jul. 26, 2020, now Pat. No. 11,580,242.

(60) Provisional application No. 62/879,224, filed on Jul. 26, 2019.

(51) Int. Cl.
| G06F 21/62 | (2013.01) |
| G06F 16/27 | (2019.01) |
| G06F 16/93 | (2019.01) |
| G06F 21/60 | (2013.01) |

(52) U.S. Cl.
CPC .......... *G06F 21/6218* (2013.01); *G06F 16/27* (2019.01); *G06F 16/93* (2019.01); *G06F 21/602* (2013.01)

(58) Field of Classification Search
CPC ...... G06F 21/6218; G06F 16/27; G06F 16/93; G06F 21/602; G06F 21/64; G06Q 10/1053; G06Q 30/018; G16H 10/60; G16H 40/20

See application file for complete search history.

(56) References Cited

U.S. PATENT DOCUMENTS

| 10,885,170 | B1* | 1/2021 | Maliani | H04L 9/0643 |
| 2011/0246460 | A1* | 10/2011 | Hsieh | G06F 16/182 |
| | | | | 709/202 |
| 2013/0030989 | A1* | 1/2013 | Geller | G06Q 10/10 |
| | | | | 705/317 |
| 2016/0119305 | A1* | 4/2016 | Panchura | H04L 63/08 |
| | | | | 726/5 |
| 2018/0082256 | A1* | 3/2018 | Tummuru | H04L 9/3236 |
| 2020/0175138 | A1* | 6/2020 | Nordstrom | H04L 9/3239 |
| 2021/0365584 | A1* | 11/2021 | Harris | H04L 67/10 |

* cited by examiner

*Primary Examiner* — Mohammed Waliullah

(57) ABSTRACT

A method for preparing a credential package includes providing access to a credential record of a plurality of credential records stored in a database system. The credential record includes information identifying a credential candidate and credential information associated with the credential candidate. The method further comprising receiving a credential document associated with the credential information, receiving credential document information associated with the credential document, and storing the credential document in a distributed ledger system comprising a plurality of nodes.

18 Claims, 8 Drawing Sheets

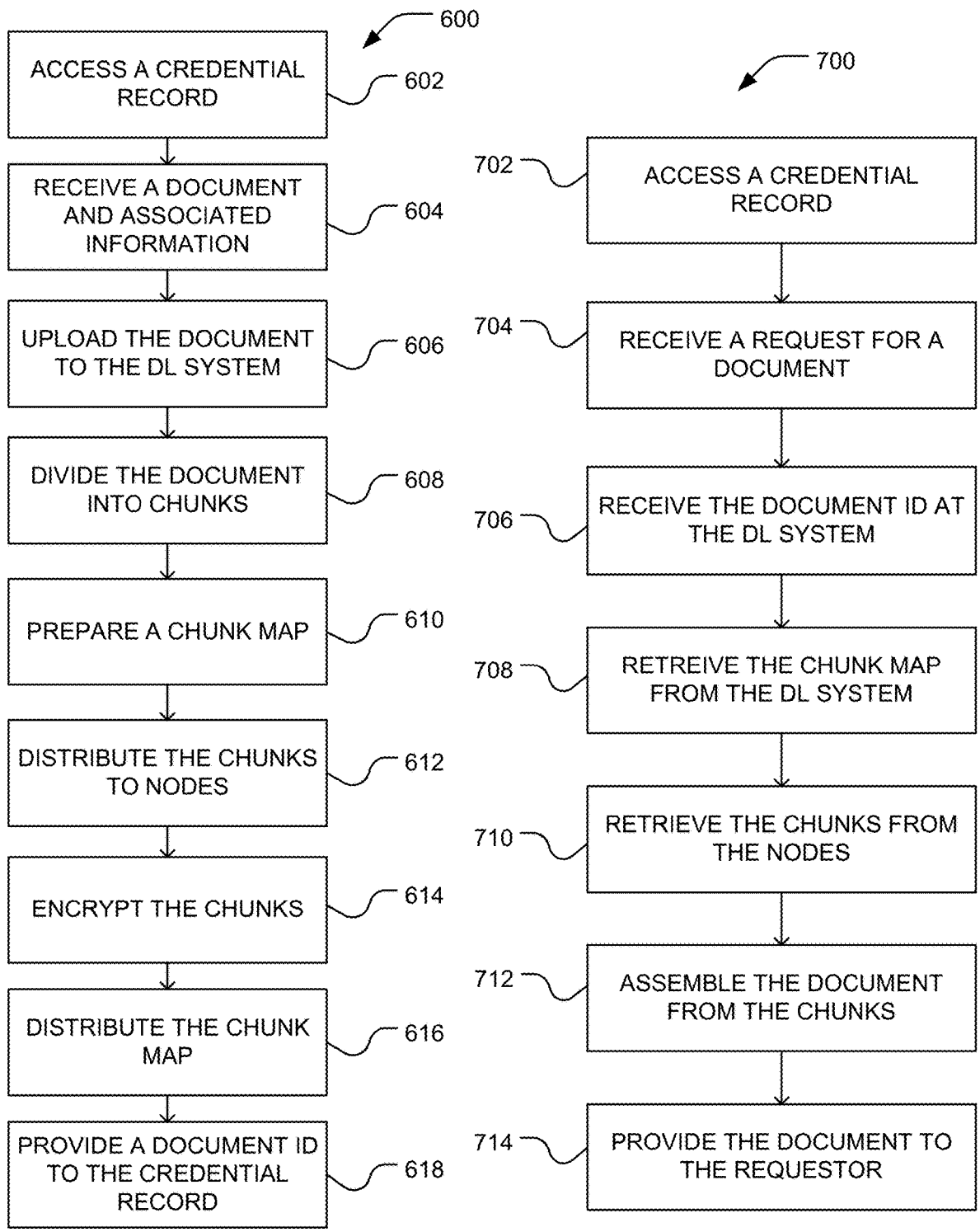

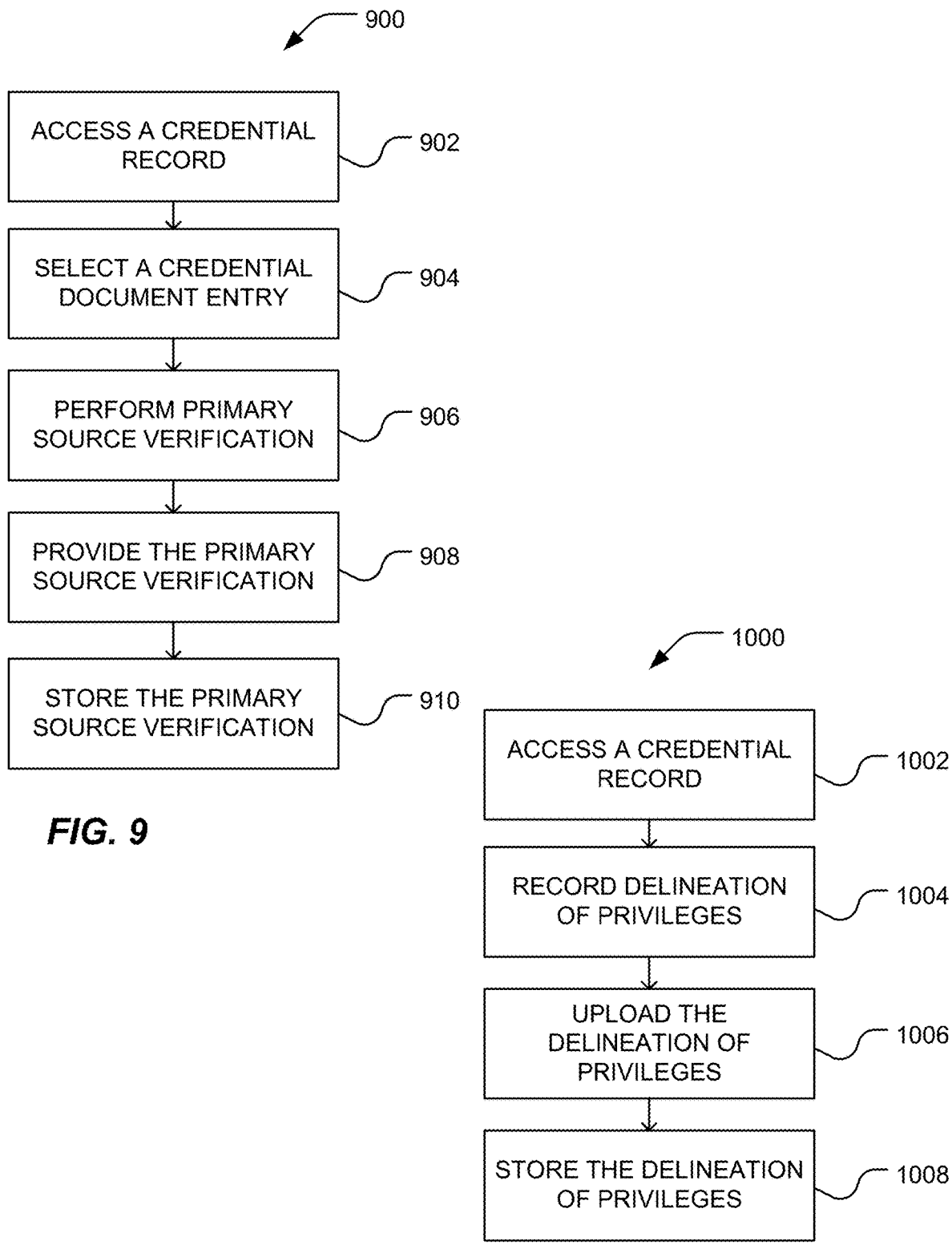

SECURE CREDENTIALING SYSTEMS AND METHODS

CROSS-REFERENCE TO RELATED APPLICATION(S)

This application is a continuation of U.S. patent application Ser. No. 16/939,037, filed Jul. 26, 2020, which claims benefit of U.S. Provisional Application No. 62/879,224, filed Jul. 26, 2019, each of which is incorporated herein by reference in its entirety.

BACKGROUND

As the economy has changed in recent years, the workforce has changed from one in which workers remain in a job for many years, in some cases through retirement, to workers more frequently changing jobs. Such job changes often come with changes in location as well. With such job mobility, there is an increased interest in verifying the credentials of potential workers or employees.

Such an interest in verifying the credentials of potential employees is particularly relevant when the employee is a licensed professional. Examples of licensed professionals include engineers, teachers, therapists, and various medical professionals.

In particular, credentialing medical professionals is an ongoing challenge for medical practices, hospitals, treatment centers, and other large organizations hiring medical professionals with various certifications and skill sets. For example, traveling emergency room doctors or traveling nurses often work under short-term contracts, such as three or six-month contracts. In another example, doctors may join a medical practice and seek surgical privileges at a hospital. As such, two organizations are performing credentialing activities with little or no insight into the actions of the other organization.

Credentialing using conventional methods can take an extended period of time, representing a large overhead expenditure when hiring a short-term employee or leading to wasteful redundant efforts. When a medical professional changes jobs, the process is repeated with no understanding of the history of the verifications and other credentialing activities performed by prior facilities.

As such, an improved credentialing system would be desirable.

BRIEF DESCRIPTION OF THE DRAWINGS

The present disclosure may be better understood, and its numerous features and advantages made apparent to those skilled in the art by referencing the accompanying drawings.

FIG. 6, FIG. 7, FIG. 8, FIG. 9, and FIG. 10 include block flow diagrams illustrating example methods for use by credentialing systems.

The use of the same reference symbols in different drawings indicates similar or identical items.

DETAILED DESCRIPTION

In an embodiment, a credentialing system provides an interface into a credential record that references documents stored in conjunction with a distributed ledger system. The distributed ledger contains a record of transactions within the credentialing system. The distributed ledger stores data across a network of computers, referred to herein as nodes. The nodes on the network verify transactions and agree with their order and existence on the ledger, referred to herein as consensus. As such, the system is capable of immutably storing documents in a decentralized system having a high degree of security. In particular, documents associated with the credentials record cannot be modified, and thus can be shown to have not been modified after being verified.

Such a system can be utilized for a variety of credentialing and verifying purposes, such as credentialing professionals or verifying an organization's history. While many uses can be envisaged, examples herein reference licensed medical professionals and associated organizations seeking to credential such licensed medical professionals. Such technology can be applied to other credentialing or verification uses.

Figure 1:
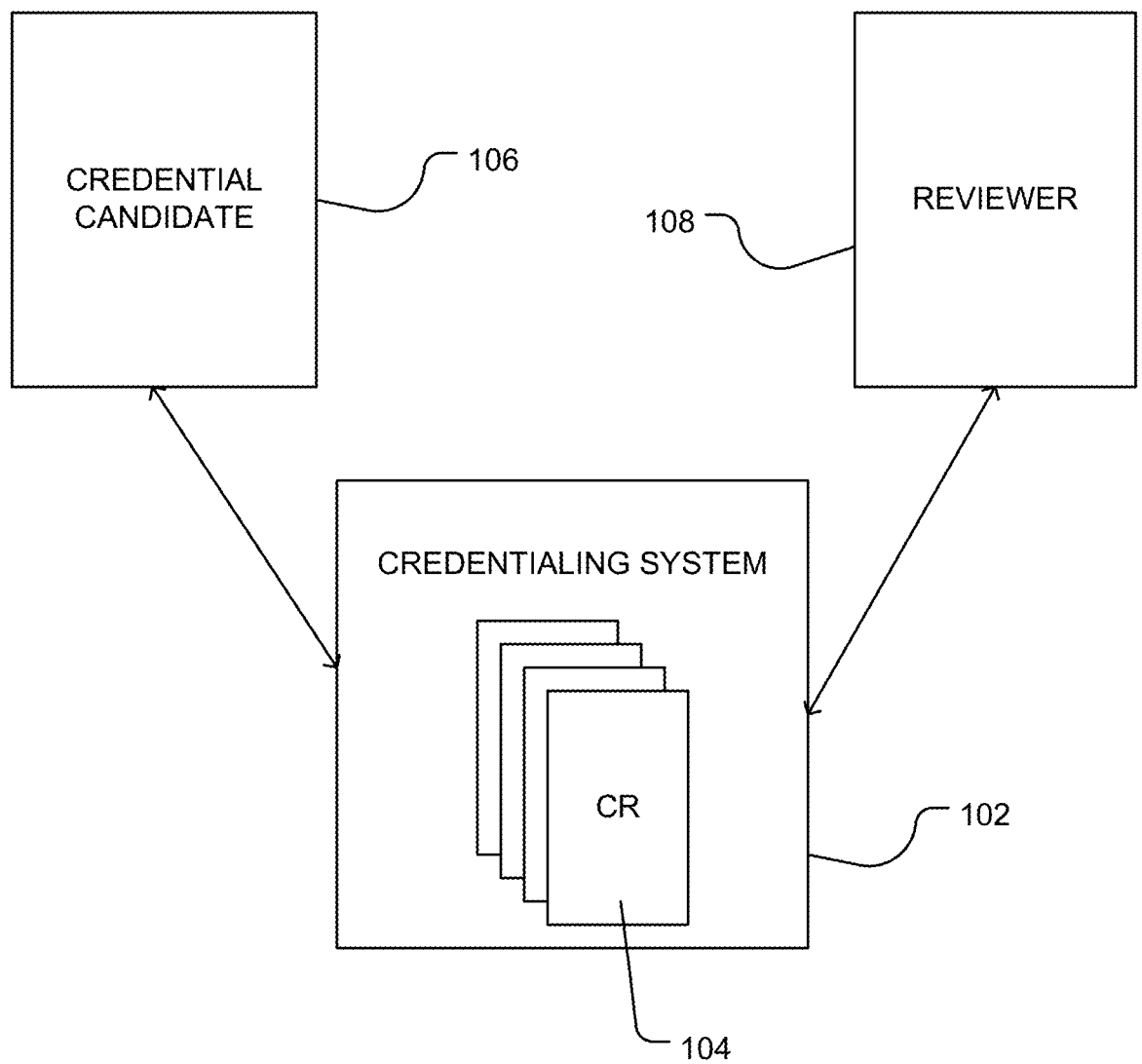
FIG. 1 includes an illustration of an example credentialing system.

For example, as illustrated in FIG. 1, a credentialing system 102 includes a set of credential records 104. A credential candidate 106 can access the credentialing system 102 to establish, modify, or update a credential record 104. The credential candidate 106 can direct the credentialing system 102 to allow access by a reviewer 108. The reviewer 108 can view the credential record 104 associated with the credential candidate 106, verify the validity of documents provided in the credential record, and delineate privileges provided to the credential candidate 106 as a result of the credentialing process.

In an example, the credential candidate 106 is a licensed medical professional who provides records showing identity, educational history, work history, experience, or licenses, among other items. A reviewer 108, such as a facilities management group of a facility or contracted by a facility, such as a practice, clinic, hospital, or center, can review the credential record, perform primary source verification, and optionally delineate which privileges the licensed medical professional is to have while working with the facility. Using the credential record, a credential candidate 106 can prepare a credentialing package to provide to the reviewer 108. For example, the credential candidate 106 can email the reviewer 108 the credential packet. In another example, the credential candidate 106 can provide access to the credential record 104 at the credentialing system 102 to the reviewer 108.

In an example, the credentialing system 102 incorporates a distributed ledger system having a plurality of nodes. The distributed ledger system can be utilized to store documents in an immutable format. A document can be a file and a set of metadata fields associated with that file. Each type of credential document can have different required metadata fields. Optionally, placeholder documents can be created which consists of metadata without a file. Documents can be added or updated by the credential candidate 106 or their designated reviewers 108. In an example, the system 102 utilizes the distributed ledger system to keep a complete history of the document.

In particular, each document is to be securely stored within the distributed ledger network. Documents can be broken down into chunks, encrypted, and distributed throughout the network. When requested, the documents can be reassembled from the chunks, decrypted, and passed back to the requester.

In some examples, the documents are associated with an expiration date. For example, an expiration date can be stored within the credential record 104 in association with the document referenced by the credential record 104. In a particular example, the documents can be displayed to the credential candidate 106 or reviewer 108 with an indication of how close the document is to expiration. In some examples, licensed professionals risk losing privileges or risk legal trouble if credentialed documents are not kept current.

Figure 2:
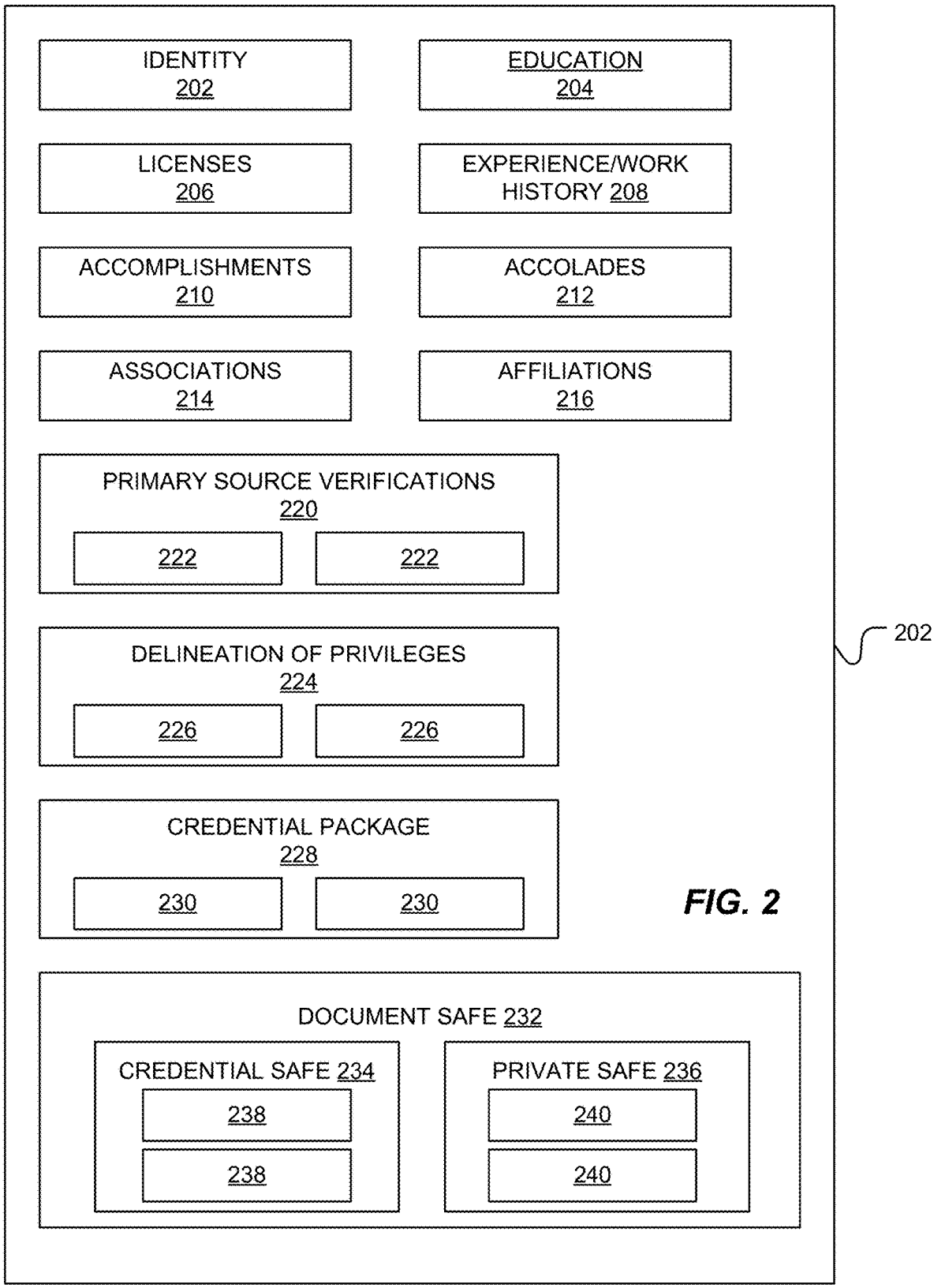
FIG. 2 includes illustration of an example credential record.

FIG. 2 includes an illustration of an exemplary credential record 200. In particular, the credential record 200 includes information regarding a candidate's identity 202, education 204, licenses 206, experience or work history 208, accomplishments 210, accolades 212, associations 214, affiliations 216, or publications 218. Documents associated with the information can be referenced in a documents safe 232. In an example, the documents safe 232 can be divided into a credentials safe 234 and a private safe 236. Documents associated with the credentials safe 234 can be accessed by reviewers 108 that the credential candidate 106 has provided with access to the records. A private safe 236 includes references to documents that are invisible to reviewers 108.

For example, the documents safe 232 may store a document or reference a document associated with the identity of a credential candidate, such as a driver's license, passport, green card, social security card, or work visa. In another example, the documents safe 232 can reference a document supporting educational information, such as a diploma or certificate. In a further example, the documents safe 232 can reference a document associated with a license, such as a license from a medical review board.

The credential candidate can allocate the documents to the credentials safe 234 or the private safe 236. For example, documents relevant to credentialing the candidate for a particular job, such as documents 238, can be referenced in the credentials safe 234. In another example, documents 240 not relevant to current credentialing efforts can be referenced by the private safe 236. For example, licenses or experience not relevant to current credentialing efforts can be referenced in the private safe 236. Documents referenced by the documents safe 232 can be stored in an immutable format using a distributed ledger system.

Primary source verifications 220 can also be captured as documents that are uploaded into the distributed ledger system. For example, a facilities management group can verify the license of a licensed medical professional by contacting the primary source of the license. Such a primary source verification can be treated as a document that is uploaded into the distributed ledger system. As such, a primary source verification document 222 referencing a document referenced by the documents safe 232 can be stored in the distributed ledger system in an immutable fashion that can be relied upon by future reviewers of the record. Moreover, as subsequent primary source verifications are made in relation to a given document stored within the system, the documents has a greater reputation as being reliable and valid.

Further, the reviewer can make a determination based on the credential record and associated documents as to which privileges are given to a licensed medical professional. Such privileges can be provided as a delineation of privileges 226, which can be referenced in a delineation of privileges section 224 of the record 200. Similarly, the delineation of privileges 226 can be treated as a document and immutably stored within the distributed ledger system. As such, packages of delineation of privileges, primary source verification, and credentials documents used in the privilege determination process can be relied upon for decision-making since the documents have been validated and cannot be modified within the distributed ledger-based storage.

In a particular example, the credentialing record 200 can include credential packages section 228 including credential packages 230. The credential packages 230 reference information and documents submitted to a reviewer, primary source verifications, and optionally delineation of privileges. For example, for a licensed medical professional to practice at a given facility, the facility undergoes a process to provide privileges. The licensed medical professionals apply for privileges by submitting information and a number of documents as part of the process. As documents are collected by the facility management group, the documents can be validated by the issuer. For example, such validation can include primary source verification. The facility management group may also determine a delineation of privileges to extend to a candidate. The documents, primary source verification, and delineation of privileges can be incorporated into a credential package 230 representing a state of the record at the time of credentialing. As such, credential packages 230 can reference an immutable set of documents and document versions despite later versions of the documents being available within document safe 232. Over time a licensed medical professional updates credentials as they expire. However, a credentialing package formed from the specific document versions and information utilized by the facilities management group in determining privileges remains unchanged.

Figure 3:
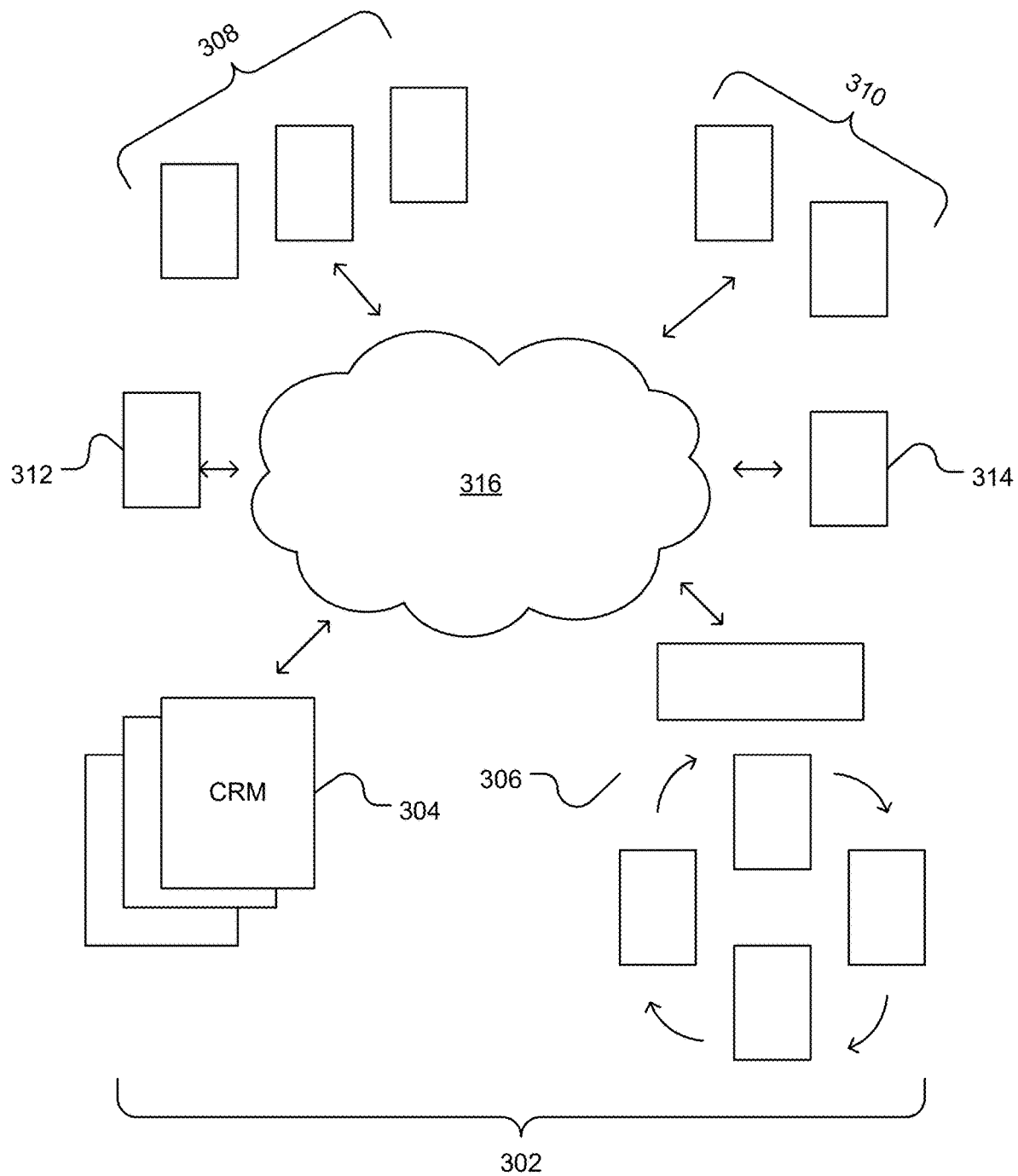
FIG. 3 includes an illustration of an example credentialing system.

In an example, the credentialing system can be implemented in a cloud-based system. For example, as illustrated in FIG. 3, a system of 302 includes a record storage system 304, such as a customer relations management system, and a distributed ledger network 306, both in communication with a network 316. Licensed medical professionals 308 interact with the record system 304 and the distributed ledger network 306 through the network 316. Similarly, facilities management groups 310 can interact with the record system 304 and distributed ledger system 306 via the network 316.

In an example, the network 316 is a global network, such as the Internet, and access to the various systems can utilize HTTP or HTTPS. Alternatively, the network 306 can be a local area network or a wide area network. Optionally, access can be provided between the various components of the system using a private or virtual private network.

Optionally, third party systems 312 or authorities 314 can be provided access to the system 302.

In particular, a licensed medical professional 308 can access the record system at 304 using a web browser, mobile application, or other software. For example, the record system 304 can serve a web-based interface to a web browser accessed by the licensed medical professionals 308. The licensed medical professionals 308 can interact with the record system 304 to form, manipulate, or update a credential record stored within the record system 304. Further, the licensed medical professionals 308 can upload documents associated with the credential record. In an example, such documents can be provided to the credential record system 304, which uploads the documents to the distributed ledger system 306. Alternatively, the credential record system 304 can direct the licensed medical professional 308 to upload the documents directly to the distributed ledger system 306.

The distributed ledger system 306 can store the documents within a peer-to-peer network, such as a private peer-to-peer network, utilizing distributed ledger technology.

The licensed medical professionals 308 can share credentials with one or more facilities management groups 310. For example, the licensed medical professional 308 can provide an email that provides a one-time share of the credential record and associated documents to a facilities management group 310. For example, the licensed medical professional 308 can select a combination of documents from his/her credentials safe to be included with the credentials record shared with the facilities management group 310. In another example, the licensed medical professional 308 can associate a credential record with a facilities management group 310. Once associated, the facilities management group 310 can have the same authority over the licensed medical professional's credentials safe as the licensed medical professional. The facilities management group 310 can add or update documents in the safe. The facilities management group 310 may not view or manage items referenced by the personal safe of the credentials record. Optionally, the facilities management group 310 can control the visibility of a subset of documents based on defined permission settings.

In an example, the record system 304 can be formed based on a customer relations management system. For example, a credentials management module can be implemented on a customer relations management (CRM) system. A client application developed over the CRM manages users and organizations and is responsible for generating alerts. The CRM system can communicate with the distributed ledger system 306 through the network 316 using, for example, HTTPS. The distributed ledger system 308 includes a plurality of nodes that verify transactions utilizing a consensus algorithm. Example distributed ledgers include blockchain, block directed acyclic graphs, transaction-based directed acyclic graphs, and hashgraph. In an example, the distributed ledge system 308 utilizes hashgraph.

Hashgraph is an alternative to blockchain that uses a gossip protocol. Every node in Hashgraph can spread signed information (called events) on newly-created transactions and transactions received from others, to its randomly chosen neighbors. These neighbors can aggregate received events with information received from other nodes into a new event and send it to other randomly chosen neighbors. This process continues until all the nodes are aware of the information created or received at the beginning. Due to the rapid convergence property of the gossip protocol, every piece of new information can reach each node in the network quickly.

Each node maintains a graph representing sequences of forwarders/witnesses for each transaction. In the ideal case, all the nodes have the same view of all transactions and their witnesses. Further, by performing virtual voting, each node can determine if a transaction is valid based on whether over two-thirds of nodes in the network have gossiped the transaction as participants or witnesses. Note that Hashgraph runs in a Byzantine setting, where the assumption is that less than a third of nodes are Byzantine (nodes that can behave badly by forging, delaying, replaying, and dropping incoming/outgoing messages). Hashgraph provides fairness via consensus time stamping. This means that if one transaction reaches two-thirds of the network ahead of other transactions, it is considered to be the first. It is a relatively fair system, as two-thirds of the network are witnesses and it is difficult for a majority of them to make unfair decisions.

In an example, the distributed ledger system can be deployed as a public network or as a private network. In a particular example, the distributed ledger system incorporates Hashgraph deployed in private, permissioned-based networks. In private distributed ledgers, identities of all nodes are known beforehand, and the network is not open to an arbitrary participant. The prior knowledge of the identities of the participating nodes provides a natural protection against Sybil attacks.

Figure 4:
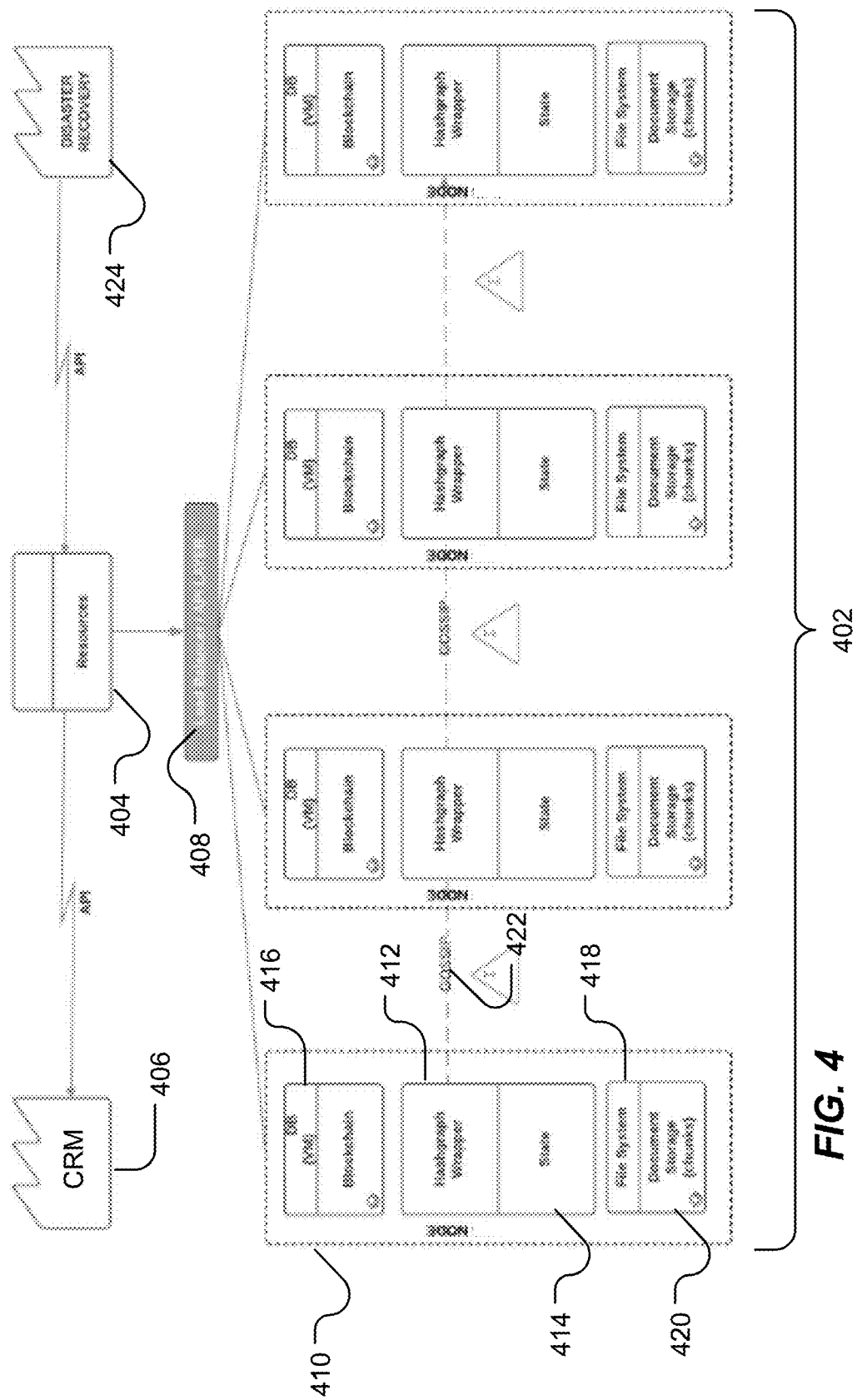
FIG. 4 includes an illustration of an example distributed ledger system.

As illustrated in FIG. 4, a distributed ledger system 400 is implemented using hashgraph to implement a consensus protocol. For example, the system 400 includes a plurality 402 of nodes 410. Each node 410 can include a Hashgraph wrapper 412 that graphs a state 414 of the system, a blockchain database 416, and a file system 418 to store document chunks 420. Transactions for which consensus has been reached can be stored in a database, such as using a blockchain, as illustrated at 416. In use, a resource 404 can communicate with the customer relations management system 406 to post and retrieve documents. Resources server 404 can interact with a load balancer/API layer 408 to access the plurality of nodes 402. With each transaction passing to and from the CRM 406 and through the resources server 404, the Hashgraph wrapper 412 of each node implements a gossip 422 between adjacent nodes or between random nodes. In accordance with the hashgraph protocol, once consensus is established through the gossips 422, the transaction is verified and stored in the blockchain 416.

In an example, the Hashgraph network serves to process and store credentials that are up-loaded by licensed medical professionals. A document is distributed to each node in chunks (shards) and validated once all nodes achieve consensus (using gossip protocol) on validity of the transaction. Each node runs on its own server image. Each node is a self-contained replica.

In an example, the hashgraph tier employs firewall techniques to restrict network traffic to the virtual servers that make up the Hashgraph Tier. HTTP traffic is restricted to HTTPS and enforces certificate authentication to ensure only authorized applications or persons are able to make API requests. As an additional security measure, the CRM hosts that run the client application are whitelisted for access to the HTTPS port. The port(s) that Hashgraph nodes are configured to use for gossip are open. Access to the ports that expose the database's API and management console are whitelisted. All unused ports are disabled.

In the illustrated example, there are a number of nodes in a Hashgraph tier. The number of nodes are set empirically to achieve maximum throughput. Each node is comprised of:

One Swirlds node or virtual machine. Hedera provides a licensed SDK (Swirlds) to develop Hashgraph applications.

The REST API is built into the Swirlds node to gossip with other nodes in the network.

A database instance, for example a NoSQL database, which serves as the block logger for its Swirlds node. This is where all transactions are logged to create a ledger. A blockchain data structure can be used to store the transaction.

Filesystem storage for documents. The filesystem storage can be located on either virtual machine, however locating it on the Swirlds virtual machine takes network performance out of the equation and makes configuring the virtual servers easier.

Optionally, an encrypted file system for storing database data, document chunks (shards) and a temporary space for attachment-related operations.

Each node can consist of two virtual machines: The Hashgraph node itself and the database instance. A single database user is created for the Hashgraph node's use. The database access credentials are unique for each node, such that node A's Hashgraph machine can only access node A's database instance. For example, node A does not have access to the database instances of any other node.

In an example, the hashgraph application architecture follows the pattern established by Hedera Hashgraph Application Framework. Handlers for REST requests are written using the Java-standard JAXRS approach. The framework can use the Grizzly web server included with Java Standard Edition to expose the endpoints. Endpoints can query (but not modify) the Hashgraph application state and the blockchain data stored in database. They can also generate Hashgraph transactions in cases where requests are intended to add or modify Hashgraph state data. These transactions are passed on to the Hashgraph platform, which distributes them throughout the network. Once the network comes to consensus on a transaction, it is processed in order by all nodes and logged to the blockchain in database.

Nearly all of the contents and their associated permissions or visibility settings are managed in the Hashgraph. Hashgraph by itself does not have built-in facilities for persisting data—everything is held in memory. An example implementation utilizes databases to ensure data is permanently persisted. Each object is identified using a UUID, which ensures uniqueness of value in a distributed computing setting. Data objects in the Hashgraph data model have been designed as "append only" databases, so that the state of the data at any given time can always be ascertained. The database could be deterministically recreated up to the point of any given transaction based on the blockchain-secured transaction log kept by the Hashgraph also in database.

Figure 5:
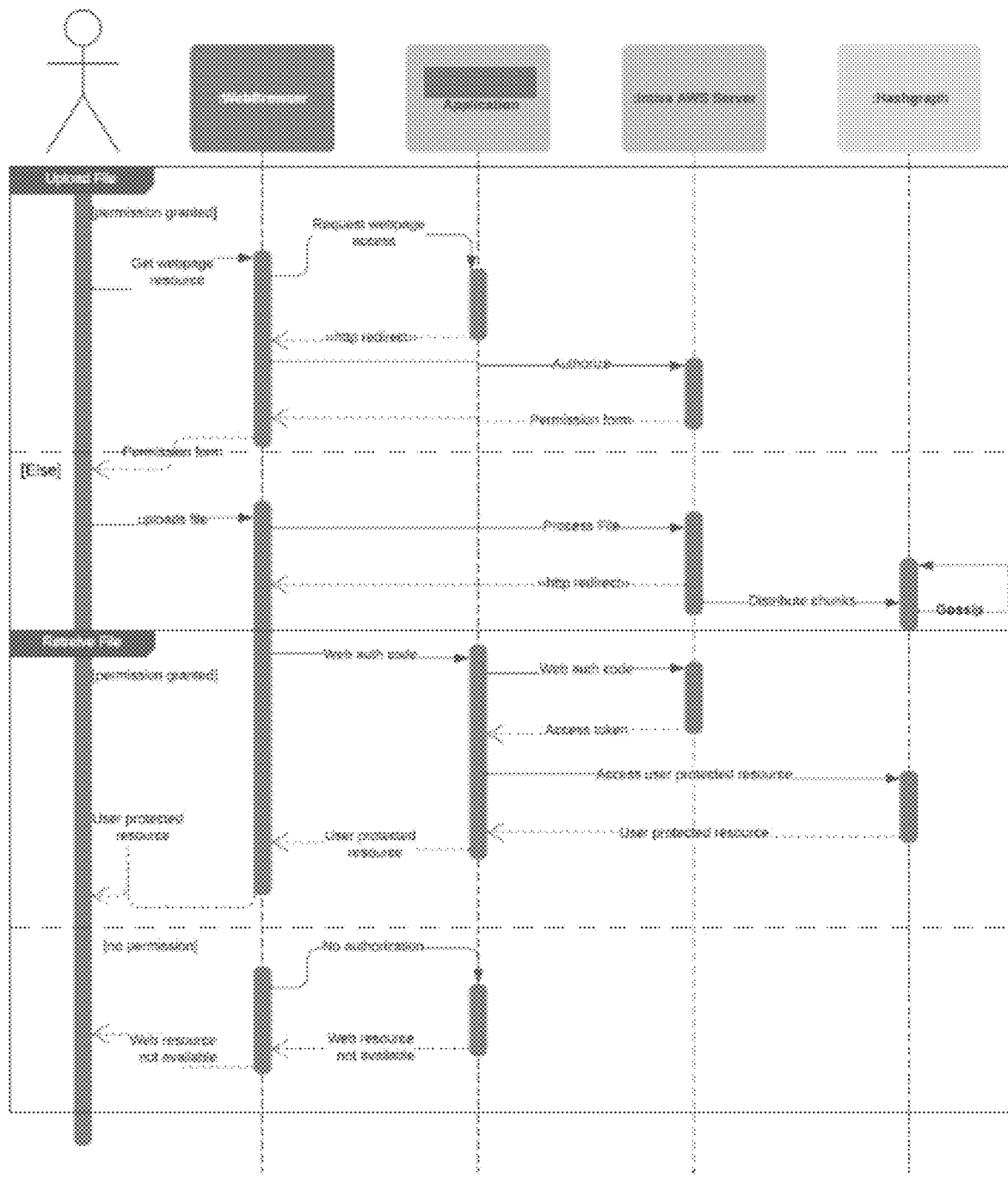
FIG. 5 includes a diagram of an example method for uploading and retrieving files.

FIG. 5, FIG. 6, and FIG. 7 include illustrations of exemplary methods for uploading and retrieving files from the distributed ledger system. For example, to upload a file, as illustrated in FIG. 6, a method 600 includes accessing a credential record, as illustrated at block 602. Such access can include requesting a webpage access from the CRM application followed by requesting authorization from the server, as illustrated in FIG. 5.

Once permission is granted, the web browser can upload the file to the CRM system or a gateway server. For example, as illustrated at block 604, the web browser can receive the document and associated information. The browser can upload the document to the distributed ledger system gateway, as illustrated at block 606. For example, as illustrated in FIG. 5, the user can upload a file that is passed to the server for processing prior to uploading to the hashgraph. Alternatively, the document can be uploaded directly to a node of the distributed ledger system acting as a master node.

As illustrated at block 608, the distributed ledger system, such as at the gateway server, can divide the document into chunks. The number of chunks can be arbitrarily selected. Alternatively, the number of chunks can be mathematically determined based on the number of nodes within the system.

As illustrated at block 610, a chunk map is prepared. For example, the chunk map can be prepared by the gateway server. Alternatively, if the document is divided by a master node, the chunk map can be prepared by the master node.

The chunks are distributed to the nodes, as illustrated at block 612. For example, the server can distribute chunks to different nodes within the network. Chunks can be stored within the file system associated with the node. In the example illustrated in FIG. 5, a server distributes the document chunks to the hashgraph. In an example, the file system is encrypted. Chunks can be encrypted for storage within the node, as illustrated at block 614.

Optionally, the chunk map is distributed to the distributed ledger network, as illustrated at block 616. For example, the chunk map can be treated as a transaction to be distributed throughout the hashgraph network and stored in response to a consensus reach about the chunk map transaction.

Optionally, a document identifier is created and provided to the credential record, system such as the CRM, as illustrated at block 618.

In an example, when a client browser requests or transmits a file, it is directly POSTed to a Hashgraph node. Direct communication between the browser and Hashgraph node(s) are secured using an access token, which is generated by a Hashgraph node during certain requests for data made by the CRM on behalf of the user and included in the payload that is passed through to the browser.

The node receives the file and invokes a manager class, which streams it to a temporary file in an encrypted directory on the node's file system. The manager then determines a hash for the file and figures out how it will break up the file for storage based on the file's size and the number of nodes in the network. That information is captured in a data object called a document shard map or chunk map. The manager breaks up the document into chunks or shards and invokes REST endpoints on the other nodes to ask them to store each shard. Connections between nodes over REST can be authenticated using X509 certificates.

Once the chunks or shards have been transferred to their destinations (other nodes), the manager creates a transaction to store the document shard map, which is passed to the Hashgraph network and processed as in "hashgraph way" (i.e., request gossips to other nodes and upon consensus commits the transaction).

To retrieve a file, the system references the chunk map and retrieves the chunks of the document. For example, as illustrated in FIG. 7, a method 700 includes accessing a credential record, as illustrated at block 702. As shown in FIG. 5, a user, through a web browser, can access the CRM system which interacts with the gateway server to acquire an access token. The CRM can access the distributed ledger nodes to retrieve the document.

Returning to FIG. 7, the gateway server can receive a request for the document, as illustrated at block 704 and, based on the access permissions, the distributed ledger system can receive the document ID, for example at a gateway or at a master node, as illustrated at block 706. The chunk map can be retrieved from the distributed ledger system, as illustrated at block 708. In particular, a gateway server can retrieve the chunk map, or a master node can retrieve the chunk map from its own memory.

As illustrated at block 710, the chunks can be received from the nodes and assembled in accordance with the chunk map, as illustrated at block 712. The document can then be provided to the credentialing system, as illustrated at block 714. In the event that a user does not have permission to retrieve a resource, the record system, such as the CRM, can prevent the associated web browser from accessing the distributed ledger system, as illustrated in FIG. 5.

For example, when a document is requested by a client, a node asks the nodes access manager to retrieve the document shard map for the requested document version. The node initiates a number of REST requests to retrieve each shard from one of the nodes that stores it. If a node is offline or fails to return the shard, the manager will try the next node until it has exhausted the list of nodes that should hold the shard. Assuming all shards are retrieved, the manager reads the shards into memory, decrypts them, and stitches the original file together from the shards. A hash is computed on the reconstructed file and compared to the original hash. A match guarantees that the reconstructed file is identical to the original file, and that the file has not been tampered with. In an example, except document upload, all other transaction are sent from the CRM, which is certificate authenticated. Read-only requests for data received by an individual node can be serviced using that node's copy of the state (database instance) and do not need to involve other nodes. A request can be made to any node, and the result will be the same.

Figure 8:
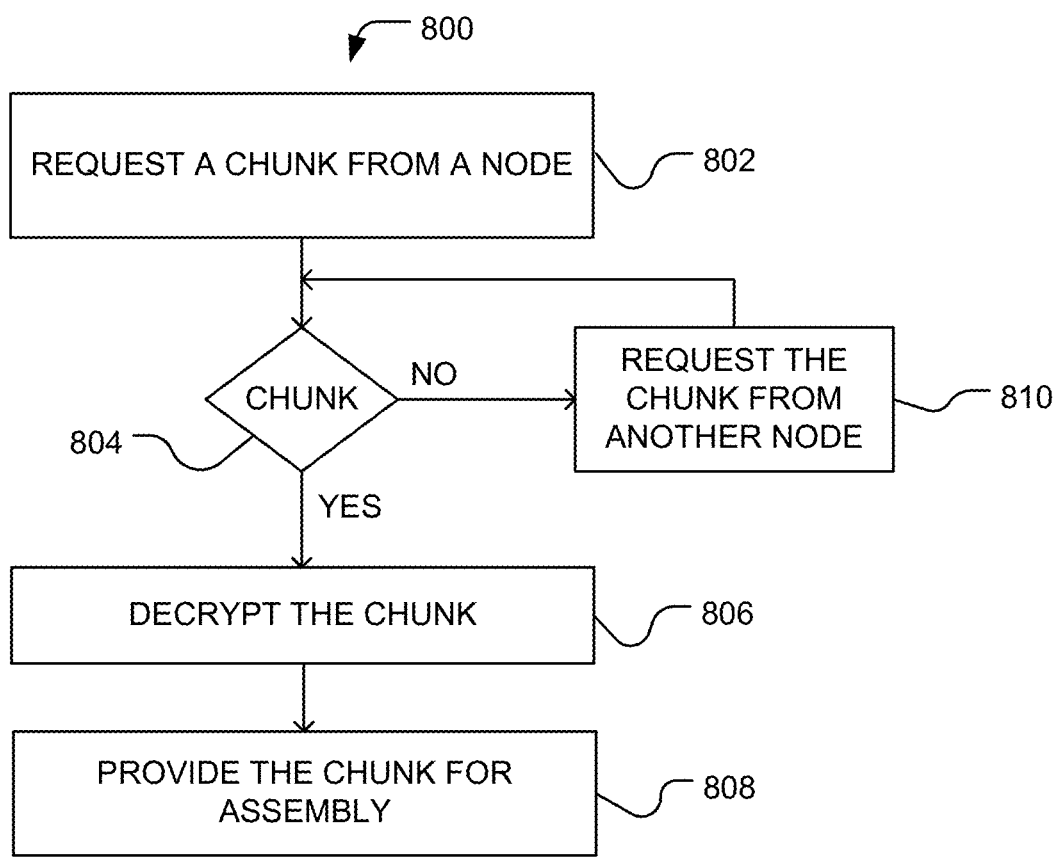

In particular, the chunks can be retrieved by requesting chunks from nodes. For example, as illustrated in FIG. 8, a method 800 includes requesting a chunk, as illustrated at block 802. For example, a node can request a chunk from another node within the system. The other node can indicate, as illustrated at block 804, whether the chunk is available from that node. If the chunk is available from that node, the chunk can be decrypted, as illustrated at block 806, and provided to the requesting node, as illustrated at block 808. If the chunk is not available at the node, another node can receive a request for the chunk, as illustrated at block 810, and the process repeated.

In a further example, verifications of a document can be stored within the distributed ledger system and as such be immutable and secure. For example, as illustrated in FIG. 9, a method 900 includes accessing a credential record, as illustrated at block 902. A user, such as a facilities management group, can select a credential document referenced within a record, as illustrated at block 904.

The facilities management group can perform primary source verification, as illustrated at block 906. For example, the facilities management group can contact the primary source of a given document and verify or confirm its validity. For example, a driver's license can be checked with the associated state Department of Motor Vehicles or Department of Public Safety. In another example, a diploma or transcript can be verified through the issuing institution.

Optionally, the facilities management group can provide the primary source verification to the system, which can treat the primary source verification as a document to be stored in the distributed ledger system, as illustrated at block 908. Following the procedure for storing a document within the distributed ledger system, the system can store the primary source verification in the distributed ledger, as illustrated at block 910. In such a way, primary source verifications associated with a given document can be stored in an immutable and time stamped format and can be relied upon by future reviewers.

Similarly, a delineation of privileges can be treated as a document stored within the distributed ledger system. For example, as illustrated in FIG. 10, method 1000 includes accessing a credential record, as illustrated at block 1002. For example, a facilities management group can access the credential record it has reviewed. Once the facilities management group makes a decision about the privileges to be extended to the licensed medical professional, a record of the delineation of privileges can be provided to the record system, as illustrated at block 1004.

The system can upload the delineation of privileges to the distributed ledger system, as illustrated at block 1006, and the system can store the delineation of privileges in the distributed ledger system, as illustrated at block 1008. In particular, the system can upload and store the delineation of privileges within the distributed ledger system utilizing a method similar to that of uploading a credentialing document.

In an example, when the credential record, a specific credential document, or a privilege delineation is requested, the system can display previous verifications or information regarding the document or delineation, such as verification date, expiration date, or an identity of the party performing the verification.

In a first aspect, a method for preparing a credential package includes providing access to a credential record of a plurality of credential records stored in a database system. The credential record includes information identifying a credential candidate and credential information associated with the credential candidate. The method further comprising receiving a credential document associated with the credential information, receiving credential document information associated with the credential document, and storing the credential document in a distributed ledger system comprising a plurality of nodes.

In an example, receiving the credential document includes receiving the credential document at a node of the distributed ledger system.

In another example of the first aspect and the above examples, storing the credential document includes dividing the credential document into a plurality of document chunks and distributing the plurality of document chunks to the plurality of nodes within the distributed ledger system. For example, document chunks of the plurality of document chunks are distributed to different nodes of the plurality of nodes. In an example, distributing the plurality of document chunks to the plurality of nodes includes sharing a document chunk of the plurality of document chunks with a first node of the plurality of nodes and sharing the document chunk from the first node of the plurality of nodes to a second node of the plurality of nodes. For example, the method further includes sharing the document chunk to additional nodes until a number of nodes greater than a Byzantine number has received the chunk.

In a further example of the first aspect and the above examples, the method further includes encrypting the document chunks prior to storing the document chunk at a node of the plurality of nodes. In an additional example of the first aspect and the above examples, storing the credential document further includes creating a document chunk map identifying and ordering the plurality of chunks and storing the document chunk map in the distributed ledger system. In another example, the method further includes storing the document chunk map at a node of the plurality of nodes when consensus about the document chunk map has been reached in accordance with a consensus protocol of the distributed ledger system. For example, the consensus protocol is implemented as a gossip protocol. In another example, the method further includes accessing the document chunk map at a node of the plurality of nodes of the distributed ledger system, retrieving the plurality of document chunks identified in the document chunk map from different nodes of the plurality of nodes, and assembling the plurality of document chunks in accordance with the document chunk map to provide the document. For example, retrieving the plurality of document chunks includes requesting with a node a document chunk from a neighbor node, and when the neighbor node does not have the requested document chunk, requesting with the node the document chunk from another neighbor node.

In an additional example of the first aspect and the above examples the database system is a customer relationship management system.

In another example of the first aspect and the above examples, the distributed ledger system utilizes a consensus protocol. In an example, the consensus protocol is implemented as a gossip protocol.

In a further example of the first aspect and the above examples, the distributed leger system utilizes a hashgraph protocol.

In an additional example of the first aspect and the above examples, the credential document information includes primary source verification associated with the credential document. For example, the method further includes storing the primary source verification in the distributed ledger system.

In another example of the first aspect and the above examples, the credential record includes a private safe and a credential safe, the private safe referencing documents stored in the distributed ledger systems, and the method further includes assigning a document from the private safe to the credential safe.

In a second aspect, a method for preparing a credential package includes providing access to a credential record of a plurality of credential records stored in a customer relation management system. The credential record includes information identifying a credential candidate and credential information associated with the credential candidate. The method further includes receiving a credential document, receiving a primary source verification associated with the credential document, and storing the credential document and the primary source verification in a distributed ledger system comprising a plurality of nodes. The credential document is divided into a plurality of document chunks. The plurality of document chunks are distributed to the plurality of nodes.

In a third aspect, a method for storing a document includes receiving a document at a distributed ledger system including a plurality of nodes, dividing the document into a plurality of chunks, creating a document chunk map identifying and ordering the plurality of chunks, distributing the plurality of chunks to different nodes of the plurality of nodes, and distributing the document chunk map to the plurality of nodes.

In an example of the third aspect, the method further includes assigning the document a document identifier. For example, the method further includes sharing the document identifier with a database separate from the distributed ledger system.

In another example of the third aspect and the above examples, the dividing the document and creating a chunk map are performed by a node of the plurality of nodes.

In a further example of the third aspect and the above examples, distributing the plurality of chunks includes sharing a chunk of the plurality of chunks with a first node of the plurality of nodes and sharing the chunk from the first node of the plurality of nodes to a second node of the plurality of nodes. For example, the method further includes sharing the chunk to additional nodes until a number of nodes greater than a Byzantine number has received the chunk.

In an additional example of the third aspect and the above examples, the method further includes storing the document chunk map at a node of the plurality of nodes when consensus about the document chunk map has been reached in accordance with a consensus protocol of the distributed ledger system. For example, the consensus protocol is implemented as a gossip protocol.

In another example of the third aspect and the above examples, the method further includes encrypting the document chunks.

In a fourth aspect, a method of retrieving a document includes accessing a document chunk map at a node of a plurality of nodes of a distributed ledger system, retrieving a plurality of document chunks identified in the document chunk map from different nodes of the plurality of nodes, and assembling the plurality of document chunks in accordance with the document chunk map to provide the document.

In an example, the method further includes decrypting each document chunk of the plurality of document chunks prior to assembling the plurality of document chunks.

In another example of the fourth aspect and the above examples, the method further includes checking the document against a hash to determine the document is intact.

In a further example of the fourth aspect and the above examples, retrieving the plurality of document chunks includes requesting from a node a document chunk from a neighbor node, the neighbor node providing the document chunk to the node. For example, the neighbor node is randomly selected from the plurality of nodes.

In an additional example of the fourth aspect and the above examples, retrieving the plurality of document chunks includes requesting from a node a document chunk from a neighbor node, when the neighbor nodes does not have the requested document chunk, requesting from the node the document chunk from another neighbor node.

In a fifth aspect, a system for credentialing includes an interface server to interact with a user; a credential database accessible to the interface server, the credential database to store a credential record associated with a credential candidate, and a distributed ledger network in communication with the interface server to store credential documents associated with the credential candidate, the distributed ledger network includes a plurality of nodes in communication with each other in a peer-to-peer network.

In an example of the fifth aspect, the credential record includes a credential safe including references to documents of a first set of documents shared with a credentialing organization and a private safe including references to documents of a second set of documents not shared with a credentialing organization.

In another example of the fifth aspect and the above examples, each node of the plurality of nodes implements a consensus algorithm and includes a file system to store the documents. For example, the consensus algorithm and the file system are implemented in a virtual machine at the node. In another example, the consensus algorithm and the file system are implemented in separate virtual machines at the node. In an additional example, each node includes a block logger to log events. In a further example, each node includes an encryption system to encrypt documents.

In a further example of the fifth aspect and the above examples, the system further includes a gateway in communication between the interface server and the distributed ledger network.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method for preparing a credential package, the method comprising:
   providing access to a credential record of a plurality of credential records stored in a database system, the credential record including information identifying a credential candidate and credential information associated with the credential candidate;
   receiving a credential document associated with the credential information;
   receiving credential document information associated with the credential document; and
   storing the credential document in a distributed ledger system comprising a plurality of nodes;
   wherein the credential record includes a private safe and a credential safe, the private safe referencing documents stored in the distributed ledger systems, the method further comprising assigning a document from the private safe to the credential safe.

2. The method of claim 1, wherein receiving the credential document includes receiving the credential document at a node of the distributed ledger system.

3. The method of claim 1, wherein storing the credential document includes:
   dividing the credential document into a plurality of document chunks; and
   distributing the plurality of document chunks to the plurality of nodes within the distributed ledger system.

4. The method of claim 3, wherein document chunks of the plurality of document chunks are distributed to different nodes of the plurality of nodes.

5. The method of claim 3, wherein distributing the plurality of document chunks to the plurality of nodes comprises:
   sharing a document chunk of the plurality of document chunks with a first node of the plurality of nodes; and
   sharing the document chunk from the first node of the plurality of nodes to a second node of the plurality of nodes.

6. The method of claim 5, further comprising sharing the document chunk to additional nodes until a number of nodes greater than a Byzantine number has received the chunk.

7. The method of claim 3, further comprising encrypting the document chunks prior to storing the document chunk at a node of the plurality of nodes.

8. The method of claim 3, wherein storing the credential document further includes:
   creating a document chunk map identifying and ordering the plurality of chunks; and
   storing the document chunk map in the distributed ledger system.

9. The method of claim 8, further comprising storing the document chunk map at a node of the plurality of nodes when consensus about the document chunk map has been reached in accordance with a consensus protocol of the distributed ledger system.

10. The method of claim 9, wherein the consensus protocol is implemented as a gossip protocol.

11. The method of claim 8, further comprising:
    accessing the document chunk map at a node of the plurality of nodes of the distributed ledger system;
    retrieving the plurality of document chunks identified in the document chunk map from different nodes of the plurality of nodes; and
    assembling the plurality of document chunks in accordance with the document chunk map to provide the document.

12. The method of claim 1, wherein the database system is a customer relationship management system.

13. The method of claim 1, wherein the distributed ledger system utilizes a consensus protocol.

14. The method of claim 13, wherein the consensus protocol is implemented as a gossip protocol.

15. The method of claim 1, wherein the distributed leger system utilizes a hashgraph protocol.

16. The method of claim 1, wherein the credential document information includes primary source verification associated with the credential document.

17. The method of claim 16, further comprising storing the primary source verification in the distributed ledger system.

18. A method for preparing a credential package, the method comprising:
    providing access to a credential record of the plurality of credential records stored in a customer relation management system, the credential record including information identifying a credential candidate and credential information associated with the credential candidate;
    receiving a credential document;
    receiving a primary source verification associated with the credential document; and
    storing the credential document and the primary source verification in a distributed ledger system comprising a plurality of nodes, the credential document divided into a plurality of document chunks, the plurality of document chunks distributed to the plurality of nodes;

wherein the credential record includes a private safe and a credential safe, the private safe referencing documents stored in the distributed ledger systems, the method further comprising assigning a document from the private safe to the credential safe.

\* \* \* \* \*